(12) United States Patent
Zhang et al.

(10) Patent No.: US 11,580,646 B2
(45) Date of Patent: Feb. 14, 2023

(54) MEDICAL IMAGE SEGMENTATION METHOD BASED ON U-NET

(71) Applicant: NANJING UNIVERSITY OF POSTS AND TELECOMMUNICATIONS, Nanjing (CN)

(72) Inventors: Dengyin Zhang, Nanjing (CN); Rong Zhao, Nanjing (CN); Weidan Yan, Nanjing (CN)

(73) Assignee: NANJING UNIVERSITY OF POSTS AND TELECOMMUNICATIONS, Nanjing (CN)

( * ) Notice: Subject to any disclaimer, the term of this patent is extended or adjusted under 35 U.S.C. 154(b) by 0 days.

(21) Appl. No.: 17/568,938

(22) Filed: Jan. 5, 2022

(65) Prior Publication Data

US 2022/0309674 A1 Sep. 29, 2022

Related U.S. Application Data

(63) Continuation of application No. PCT/CN2021/137909, filed on Dec. 14, 2021.

(51) Int. Cl.
*G06K 9/62* (2022.01)
*G06T 7/11* (2017.01)
*G06T 3/40* (2006.01)
*G06N 3/04* (2023.01)
(Continued)

(52) U.S. Cl.
CPC ............... *G06T 7/11* (2017.01); *G06N 3/0454* (2013.01); *G06N 3/088* (2013.01); *G06T 3/40* (2013.01);
(Continued)

(58) Field of Classification Search
CPC ... G06T 7/11; G06T 3/40; G06T 2207/20076; G06T 2207/20081; G06T 2207/20084;
(Continued)

(56) References Cited

U.S. PATENT DOCUMENTS 9,600,890 B2 3/2017 Dai et al.
2014/0198963 A1 7/2014 Kim et al.
(Continued)

FOREIGN PATENT DOCUMENTS

CN 108268870 A * 7/2018 ............. G06K 9/342
CN 108596915 A 9/2018
(Continued)

OTHER PUBLICATIONS

Internation Search Report of PPCT/CN2021/137909, dated Feb. 21, 2022.

*Primary Examiner* — Xin Jia

(57) ABSTRACT

A medical image segmentation method based on a U-Net, including: sending real segmentation image and original image to a generative adversarial network for data enhancement to generate a composite image with a label; then putting the composite image into original data set to obtain an expanded data set, and sending the expanded data set to improved multi-feature fusion segmentation network for training. A Dilated Convolution Module is added between the shallow and deep feature skip connections of the segmentation network to obtain receptive fields with different sizes, which enhances the fusion of detail information and deep semantics, improves the adaptability to the size of the segmentation target, and improves the medical image segmentation accuracy. The over-fitting problem that occurs when training the segmentation network is alleviated by using the expanded data set of the generative adversarial network.

8 Claims, 2 Drawing Sheets

(51) Int. Cl.
*G06N 3/088* (2023.01)
*G16H 30/40* (2018.01)

(52) U.S. Cl.
CPC ... *G16H 30/40* (2018.01); *G06T 2207/20076* (2013.01); *G06T 2207/20081* (2013.01); *G06T 2207/20084* (2013.01); *G06T 2207/20092* (2013.01); *G06T 2207/30004* (2013.01)

(58) Field of Classification Search
CPC .......... G06T 2207/20092; G06T 2207/30004; G06N 3/0454; G06N 3/088; G16H 30/40
See application file for complete search history.

(56) References Cited

U.S. PATENT DOCUMENTS

2021/0012162 A1* 1/2021 Huang ................. G06K 9/6298
2021/0264613 A1* 8/2021 Wang .................... G06V 10/26

FOREIGN PATENT DOCUMENTS

| CN | 109690554 | A | * | 4/2019 | ........... G06K 9/0014 |
|----|-----------|---|---|--------|-----|
| CN | 110570431 | A | | 12/2019 | |
| CN | 110490880 | A | | 2/2020 | |
| CN | 110807762 | A | | 2/2020 | |
| CN | 2020077202 | A1 | | 4/2020 | |
| CN | 111681252 | A | | 9/2020 | |
| CN | 111968138 | A | | 11/2020 | |
| CN | 112419327 | A | * | 2/2021 | |
| CN | 112446891 | A | | 3/2021 | |
| CN | 112950639 | A | | 6/2021 | |
| CN | 113077471 | A | | 7/2021 | |
| WO | 2020109630 | A1 | | 6/2020 | |

\* cited by examiner

MEDICAL IMAGE SEGMENTATION METHOD BASED ON U-NET

CROSS-REFERENCE TO RELATED APPLICATIONS

This application is a continuation of International Patent Application No. PCT/CN2021/137909 with a filing date of Dec. 14, 2021, designating the United States, now pending, and further claims priority to Chinese Patent Application No. 202110325496.X with a filing date of Mar. 26, 2021. The content of the aforementioned applications, including any intervening amendments thereto, are incorporated herein by reference.

TECHNICAL FIELD

The present disclosure relates to a medical image segmentation method based on a U-Net, which relates to the technical field of image processing.

BACKGROUND

The medical image segmentation technology is developed from manual segmentation to man-machine semi-automatic segmentation, and then gradually developed to a fully automatic segmentation. The manual segmentation refers to the fact that a clinician with rich experience directly outlines the boundary of the tissue or the area of interest on the original film. The manual segmentation has high requirements on the prior knowledge of people, and it takes a long time and has a high cost. With the development of deep learning in computer vision field, the semi-automatic segmentation technology has emerged. The semi-automatic segmentation technology combines data storage and calculation function of computer and the experience and knowledge of medical experts to complete the image segmentation by means of human-computer interaction. The fully automatic segmentation means that the computer runs independently and automatically completes the whole process of image segmentation according to a pre-programmed algorithm. However, the realization of most fully automatic segmentation algorithms is complicated, the segmentation results are not ideal, and the speed and performance of segmentation need to be improved. In present clinical medicine, research on practical automatic segmentation methods to replace tedious manual segmentation or semi-automatic segmentation has always been the goal pursued by people. The fully automatic segmentation method is the research focus and key technology of medical images in recent years. In order to enable the machine to automatically segment medical images, reduce tedious manual work, and lay a solid foundation for subsequent tumor recognition and pathological judgment, it is important to study how to make the segmentation edge results more accurate.

Current image segmentation methods can be divided into traditional image segmentation methods and image segmentation based on deep learning. The traditional image segmentation methods include threshold-based segmentation methods, region-based segmentation methods, and boundary-based segmentation methods. The traditional image segmentation methods mainly use edges and algorithm characteristics for segmentation, and it is easy to ignore the deep semantic category information of the image. In recent years, deep learning has made great progress in the field of computer vision, and some are gradually approaching human judgment. Therefore, the use of deep learning method for image segmentation has gradually become the mainstream. The deep learning method has no prior knowledge restrictions and can obtain good results when the network is well trained. Since the fully convolutional network proposed to use 1×1 convolution instead of the fully connected layer, medical image segmentation has shown better performance in the U-Net. Since then, the improvement of the segmentation network is mostly based on the structure of encoding-decoding-skip connection. In order to reduce the loss of information in the process of encoding and sampling, the DeepLab proposes the Atrous Spatial Pyramid Pooling (ASPP), and uses conditional random fields to optimize the segmentation results. Some networks excel at 3D segmentation like V-net, H-dense Net, etc. In order to fully integrate the feature information of different levels and different scales in the segmentation process, various segmentation models are still emerging in endlessly.

However, in the current medical image segmentation field, due to issues such as patient privacy protection, the data set is still difficult to obtain, the number of images is small, and the over-fitting problem is prone to occur when training the segmentation model, that is, the segmentation effect is better on the training set and worse on the testing set, which leads to the weak application of the model. Therefore, how to obtain an effective data set is also a major difficulty in the current research on medical image segmentation. The use of generative adversarial networks to generate composite image to expand the data sets is a major current development trend. In addition, a lot of shallow spatial and detailed information is lost due to the continuous "convolution-pooling" operation in the neural network, it is easy to cause poor segmentation effect of small lesions or organ edges. The overall segmentation effect is not good when the size difference of the required segmentation target (organ or lesion) is large. How to integrate the characteristics of the segmentation target at different scales is also the direction of current efforts of scholars. The improvement and optimization of U-Net is a research hotspot in the field of medical image segmentation.

SUMMARY

The technical problem to be solved by the present disclosure is to overcome the shortcomings of the prior art that the amount of medical image data is small and manual labeling is relatively difficult, and to provide a medical image segmentation method based on a U-Net, which increases the generative adversarial network before the original segmentation network to expand of data, and reduces the over-fitting phenomenon caused by less training data in the process of training the segmentation model. The disclosure proposes a multi-scale feature fusion segmentation method, which can reduce the semantic gap that may occur when shallow network and deep network are connected in U-Net and the problem of shallow information loss in the sampling process under max-pooling, fully capture the target regions of different sizes, and improve the segmentation accuracy of segmentation targets of different scales.

In order to achieve the above objective, the present disclosure provides a medical image segmentation method based on a U-Net, including following steps:

step 1: selecting a medical image data set from existing medical image database;

step 2: obtaining paired original image and a real segmentation map of a target area in the original image from the medical image data set; and generating, by the real segmentation map, a composite image based on a generator G;

sending the composite image to a discriminator D for discrimination; and judging, by the discriminator D, whether the composite image comes from the medical image data set, and outputting a probability that the composite image comes from the medical image data set;

step 3: importing the paired original image and the real segmentation map of the target area in the original image into a generative adversarial network to train the generative adversarial network to obtain a generator model; wherein a generative adversarial joint loss function of the generative adversarial network is:

$$\mathcal{L}(G,D)=E_{x,y}[\log D(x,y)]+E_{x,z}[\log(1-D(x,G(x,z))],$$

wherein, x is the real segmentation map of the original image, y is the original image, z is random noise, E[*] represents an expected value of a distribution function, and D(x,y) is an output probability of the discriminator D when input is x and y, G(x,z) is the composite image;

increasing distance loss of L1 to constrain a difference between the composite image and the original image and reduce fuzz:

$$\mathcal{L}_{L1}(G)=E_{x,y,z}[\|y-G(x,z)\|_1];$$

step 4: using the generator model trained in step 3 to generate the composite image; wherein the composite image and the original image are used as an input data set of a mufti-feature fusion segmentation network; and dividing the input data set into a training set and a testing set;

step 5: using the input data set in step 4 to train the multi-feature fusion segmentation network to obtain a segmentation network model; wherein, in a decoding process of the multi-feature fusion segmentation network, each decoder layer is connected to a feature map of shallow and same layer from an encoder via an Dilated Convolution Module;

step 6: inputting the original image to be segmented into the trained segmentation network model for segmentation to obtain a real segmentation image.

Preferably, in step 3, the training of the generative adversarial network comprises a training of the generator G and a training of the discriminator D; a forward propagation and backward propagation of neural network are used to alternately train the discriminator D and the generator G by gradient descent method until a probability that the composite image generated by the generator G is a real image is identified by the discriminator D as 0.5, the training is completed, and generator model and discriminator model are obtained.

Preferably, in step 5, the multi-feature fusion segmentation network comprises feature extraction and resolution enhancement; the feature extraction comprises five convolutional blocks and four down-sampling, and the convolutional blocks are connected by the down-sampling; the resolution enhancement comprises four convolutional blocks connected by up-sampling.

Preferably, step 5 comprises following steps:

in the multi-feature fusion segmentation network, setting the loss function as a set similarity measurement function, and a specific formula is:

$$\text{Dice} = \frac{2|A \cap B|}{|A|+|B|},$$

wherein, |A∩B| represents common elements between set A and set B, |A| represents a number of elements in the set A, |B| represents a number of elements in the set B, and the set A is a segmented image obtained by segmenting the input data set by the multi-feature fusion segmentation network, elements in the set B are the real segmentation image of the target area in the original image;

approximating the |A∩B| as a point multiplication between an actual segmented image and the real segmentation image to calculate a set similarity measurement function of a predicted real segmentation image;

adding all element values in a result of the point multiplication; stopping training when the loss function is minimized, sand obtaining the trained segmentation network model.

Preferably, the generator G is a codec structure, in which residual blocks of same level are skip connected in a manner like U-net; the generator G comprises 9 residual blocks, 2 down-sampled convolutional layers with a stride of 2, and 2 transposed convolutions;

after all non-residual blocks, a batch normalization function and a Relu function are executed, the discriminator D uses Markovian discriminator model which is same as patchGAN.

Preferably, a connection sequence in the convolutional block is a 3×3 convolutional layer, a batch normalization layer, a Relu activation function, a 3×3 convolutional layer, a batch normalization layer, and a Relu activation function, each down-sampling uses a max-pooling with a stride of 2, a feature map size of the original image after the convolutional layer becomes half of a feature map size of the original image before down-sampling, and a number of feature map channels of the original image becomes twice a number of feature map channels of the original image before down-sampling; up-sampling uses bilinear interpolation to double a resolution of the feature map of the original image;

in all convolutional layers, first and last convolutional layers use 7×7 convolutional kernels, and other convolutional layers use 3×3 convolutional kernels; the 7×7 convolutional kernels use separable convolution to reduce parameters of the segmentation network model and calculation amount of the segmentation network model.

Preferably, the step of stopping training when the loss function is minimized, and obtaining a trained segmentation network model, comprises following steps:

initializing weight parameters of the multi-feature fusion segmentation network at each stage based on Adam optimizer, and randomly initializing the weight parameters by using a Gaussian distribution with an average value of 0;

for each sample image in the training set input in the segmentation network model, calculating a total error between the real segmentation image and the real segmentation map of the target area in the original image by using the forward propagation first; then calculating partial derivative of each weight parameter by using the backward propagation of the neural network; and finally updating the weight parameter according to the gradient descent method; and repeating above steps to minimize the loss function to obtain the trained segmentation network model; wherein the sample image comprises the composite image and the original image.

Preferably, the input data set used as the multi-feature fusion segmentation network together with the original image is divided into the training set and the testing set in a ratio of 7:3.

The present disclosure achieves the following beneficial effects:

First, in real life, in order to protect the privacy of patients, the data set is difficult to obtain. In the present disclosure, the real segmentation image and the original image are first sent to the generative adversarial network for data enhancement, and a composite image with a label is generated; and then the composite image is put into the original data set to obtain an expanded data set, and the expanded data set is sent to an improved multi-feature fusion segmentation network for training. A Dilated Convolution Module configured to acquire receptive fields of different sizes is added between the shallow and deep feature skip connections of the segmentation network to enhance the fusion of detail information and deep semantics, improve the adaptability to the size of segmentation target, and improve the accuracy of medical image segmentation. By using the generative adversarial network to expand data set, the over-fitting problem occurred during training the segmentation network is eased, loss of details catching capability of the traditional U-Net and the problem of incomplete information characteristics of deep and shallow layers are recovered from the perspective of multi-scale feature connection, which enhances the adaptability to different segmentation task, improves the final segmentation result. Before image segmentation, the trained generator is used to generate a composite fundus vascular image, and the data set sent into the segmentation network is expanded, so as to improve the problem of over-fitting of the training data and poor effect on the required segmentation task caused by too little data in the common segmentation network.

Second, in the multi-scale feature fusion segmentation network used in the present disclosure, shallow spatial features and deep semantics are connected through multi-scale Dilated Convolution Module, which improves the semantic gap problem caused by direct connection in the original U-net, enhances the extraction of detailed information, and improves the fusion effect of feature maps at different levels.

Third, convolutional kernels with different dilate rates are used to improve the problem of small receptive fields and insufficient image feature extraction when using small convolutional kernels. The feature mappings under different receptive fields are fused to enhance the extraction of the segmentation targets at various scales. Different scale information is used to improve the accuracy of segmentation.

DETAILED DESCRIPTION OF PREFERRED EMBODIMENTS

Figure 1:
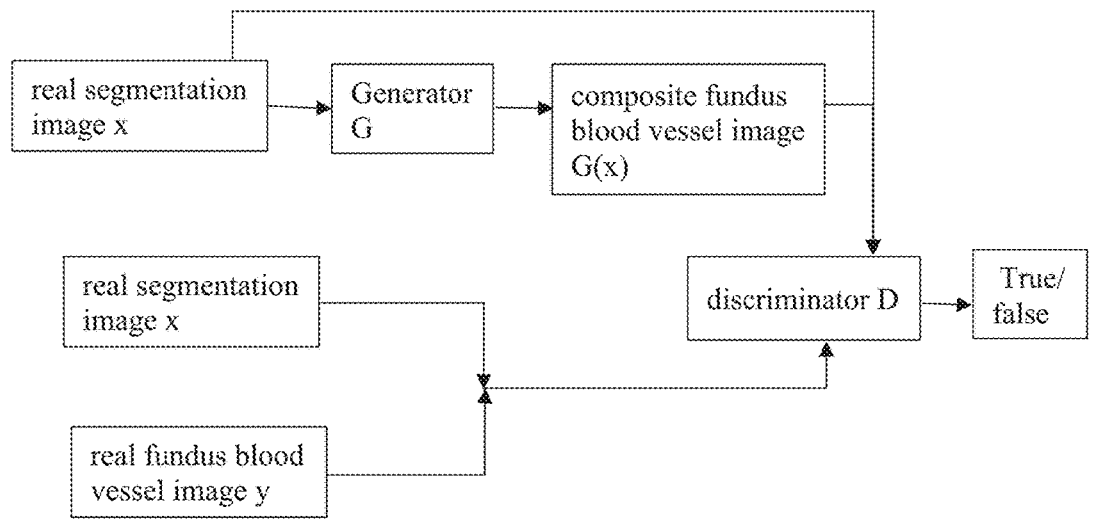
FIG. 1 is a schematic diagram of a generative adversarial network in the method of the present disclosure.

The following embodiments are only used to illustrate the technical solutions of the present disclosure more clearly, and do not limit the protection scope of the present disclosure.

The present disclosure provides a medical image segmentation method based on a U-Net, including following steps:

step 1: selecting a medical image data set from existing medical image database;

step 2: obtaining paired original image and real segmentation map of a target area in the original image from the medical image data set; and generating, by the real segmentation map, a composite image based on a generator G;

sending the composite image to a discriminator D for discrimination; and discriminating, by the discriminator D, whether the composite image comes from the medical image data set, and outputting a probability that the composite image comes from the medical image data set;

step 3: importing the paired original image and the real segmentation map of the target area in the original image into a generative adversarial network to train the generative adversarial network to obtain a generator model; wherein a generative adversarial joint loss function of the generative adversarial network is:

$$\mathcal{L}(G,D)=E_{x,y}[\log D(x,y)]+E_{x,z}[\log(1-D(x,G(x,z))],$$

wherein, x is the real segmentation map of the original image, y is the original image, z is random noise, E[*] represents an expected value of a distribution function, and D(x,y) is an output probability of the discriminator D when input is x and y, G(x,z) is the composite image;

increasing distance loss of L1 to constrain a difference between the composite image and the original image and reduce fuzz:

$$\mathcal{L}_{L1}(G)=E_{x,y,z}[\|y-G(x,z)\|_1];$$

step 4: using the generator model trained in step 3 to generate the composite image; wherein the composite image and the original image are used as an input data set of a multi-feature fusion segmentation network; and dividing the input data set into a training set and a testing set;

step 5: training the multi-feature fusion segmentation network by using the input data set in step 4 to obtain a segmentation network model; wherein, in a decoding process of the multi-feature fusion segmentation network, each decoder layer is connected to a feature mapping of shallow and same layer from an encoder via an Dilated Convolution Module;

step 6: inputting the original image to be segmented into the trained segmentation network model for segmentation to obtain a real segmentation image.

Further, in step 3, the training of the generative adversarial network comprises a training of the generator G and a training of the discriminator D; a forward propagation and backward propagation of neural network are used to alternately train the discriminator D and the generator G by gradient descent method until a probability that the composite image generated by the generator G is a real image is identified by the discriminator D as 0.5, the training is completed, and the generator model and a discriminator model are obtained.

Further, in step 5, the multi-feature fusion segmentation network comprises feature extraction and resolution enhancement; the feature extraction comprises five convolutional blocks and four down-sampling, and the convolutional blocks are connected by the down-sampling; the resolution enhancement comprises four convolutional blocks connected by up-sampling.

Further, step 5 comprises following steps:

in the multi-feature fusion segmentation network, setting a loss function as a set similarity measurement function, and a specific formula is $$\text{Dice} = \frac{2|A \cap B|}{|A|+|B|},$$

wherein, |A∩B| represents common elements between set A and set B, |A| represents a number of elements in the set A, |B| represents a number of elements in the set B, and the set A is a segmented image obtained by segmenting the input data set by the multi-feature fusion segmentation network, elements in the set B are the real segmentation image of the target area in the original image;

approximating the |A∩B| as a point multiplication between an actual segmented image and the real segmentation image to calculate the set similarity measurement function of a predicted real segmentation image; adding all element values in a result of the point multiplication; stopping training when the loss function is minimized, and obtaining the trained segmentation network model.

Further, the generator G is a codec structure, in which residual blocks of same layer are skip connected in a manner like U-net; the generator G comprises 9 residual blocks, 2 down-sampled convolutional layers with a stride of 2, and 3 transposed convolutions;

after all non-residual blocks, a batch normalization function and a Relu function are executed; the discriminator D uses Markovian discriminator model which is same as patchGAN.

Further, a connection order in the convolutional blocks is a 3×3 convolutional layer, a batch normalization layer, a Relu activation function, a 3×3 convolutional layer, a batch normalization layer, and a Relu activation function; each down-sampling uses a max-pooling with a stride of 2, a feature map size of the original image after the convolutional layer becomes half of a feature map size of the original image before down-sampling, and a number of feature map channels of the original image becomes twice of a number of feature map channels of the original image before down-sampling; up-sampling uses bilinear interpolation to double a resolution of the feature map of the original image;

in all convolutional layers, first and last convolutional layers use 7×7 convolutional kernels, and other convolutional layers use 3×3 convolutional kernels; the 7×7 convolutional kernels use separable convolution to reduce parameters of the segmentation network model and calculation amount of the segmentation network model.

Further, the step of stopping training when the loss function is minimized, and obtaining a trained segmentation network model, comprises following steps:

initializing weight parameters of the multi-feature fusion segmentation network at each stage based on Adam optimizer, and randomly initializing the weight parameters by using a Gaussian distribution with an average value of 0;

for each sample image in the training set input in the segmentation network model, calculating a total error between the real segmentation image and the real segmentation map of the target area in the original image by using the forward propagation first; then calculating partial derivative of each weight parameter by using the backward propagation of the neural network; and finally updating the weight parameter according to the gradient descent method; and repeating above steps to minimize the loss function to obtain the trained segmentation network model; wherein the sample image comprises the composite image and the original image.

Further, the input data set used as the multi-feature fusion segmentation network together with the original image is divided into the training set and the testing set in a ratio of 7:3.

Step 1, the medical image data set is obtained, wherein the medical image data set is a DRIVE fundus vascular data set.

The medical image data set is downloaded from the existing medical image database. The website address is: https://aistudio.baidu.com/aistudio/projectdetail/462184.

Paired original image of fundus blood vessels and a real segmentation map of a target area in the original image of fundus blood vessels are obtained from the medical image data set; and the composite image is generated by the real segmentation map based on the generator G.

The composite image is sent to the discriminator D for discrimination; it is judged by the discriminator D whether the composite image comes from the medical image data set, and the probability that the composite image comes from the medical image data set is output. There are many methods that can be used for this step in the prior art, and this embodiment does not give examples one by one.

Step 2, the paired original image of fundus blood vessels and the real segmentation map of the target area in the original image of fundus brood vessels are extracted from the DRIVE fundus vascular data set and input into the generative adversarial network.

The generative adversarial network uses pix2pix algorithm. A real segmented label image x is used as the input of the generator G to obtain the generated image G(x), and then the G(x) and x are merged together based on the channel dimension, and finally used as the input of the discriminator D to obtain a predicted probability value, the predicted probability value indicates whether the input is a pair of real images, the closer the probability value is to 1, the more certain that the input is a real pair of images. In addition, the real images y and x are also merged together based on the channel dimension, and used as the input of the discriminator D to obtain the probability prediction value.

Step 3, the loss function is created. The joint loss function of generator and the discriminator is:

$$\mathcal{L}(G,D)=E_{x,y}[\log D(x,y)]+E_{x,z}[\log(1-D(x,G(x,z))],$$

wherein, x is the real segmentation map of the original image, y is the original image, z is random noise, E[*] represents an expected value of a distribution function, and D(x,y) is an output probability of the discriminator D when input is x and y, G(x,z) is the composite image.

The distance loss of L1 is increased to constrain a difference between the composite image and the original image and reduce fuzz:

$$\mathcal{L}_{L1}(G)=E_{x,y,z}[\|y-G(x,z)\|_1];$$

wherein, x is a segmentation label, y is a real fundus blood vessel image, and z is random noise. The dropout is used to generate the random noise.

Total objective function is $$F = \arg\min_G \max_D \mathcal{L}_{cGAN}(G, D) + \lambda\mathcal{L}_{L1}(G).$$

Figure 2:
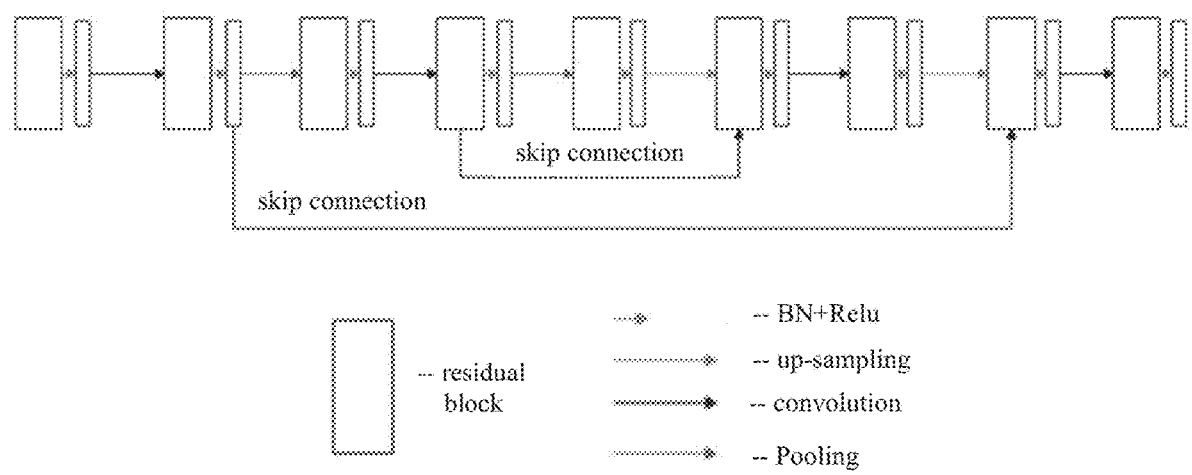
FIG. 2 is a schematic diagram of a generator in the generative adversarial network in the method of the present disclosure.

Step 4, the generative adversarial network is trained. The generative adversarial network adopts the pix2pix algorithm, and includes a generator G and a discriminator D. The generator G is in a codec structure, as shown in FIG. 2, is skip connected in a manner like U-net, and includes 9 residual blocks, 2 down-sampled convolutional layers with a stride of 2, and two transposed convolutions. The 9 residual blocks are connected in sequence, after all non-residual blocks, the batch normalization function and the Relu function are executed. The discriminator D uses Markovian discriminator model which is same as patchGAN. The Batch Normalization, is abbreviated as BN.

All convolutional layers use 3×3 convolutional kernels except for the first and last layers that use 7×7 convolutional kernels. Wherein, the 7×7 convolutional kernel uses separable convolution to reduce model parameters and calculation amount.

The input of the generator of the generative adversarial network is an image with labeled data set, and the output is the composite image of fundus blood vessel. The generator of the generative adversarial network is trained, number of iterations is M, and M is a positive integer of at least 400. The former learning rate is α, and the value of α is 0<α<0.01, and the latter learning rate decreases linearly.

The discriminator for training the generative adversarial network uses the composite image of fundus blood vessel output by the generator of the generative adversarial network and the corresponding label as the input of the discriminator of the generative adversarial network. The discriminator discriminates whether the fake image output by the generator is a real image, and the discriminator of the generative adversarial network is trained, iterates N times, N is an even number of at least 300, the former learning rate is β, the value of β is 0<β<0.001, and the subsequent learning rate decreases linearly.

The discriminator and generator are alternately trained until the probability that the fake image generated by the generator is discriminated by the discriminator as 0.5, the training ends, and the generator model and the discriminator model of the generative adversarial network are obtained.

Step 5, the multi-feature fusion segmentation network is trained by using the input data set in step 4. The multi-feature fusion segmentation network includes feature extraction and resolution enhancement. In a decoding process of the multi-feature fusion segmentation network, each decoder layer is connected to a feature mapping of shallow and same layer from an encoder via an Dilated Convolution Module to obtain the detailed information of shallow layer of different receptive fields, and which is combined with the deep semantics to improve the segmentation accuracy of the segmentation target with different sizes. The trained generator is used to generate a composite fundus blood vessel image with input labels, which is added to the original data set; the expanded data set is divided into the testing set and a verification set at a ratio of 7:3, and the two sets are then input into the segmentation network of the present disclosure (as shown in FIG. 2).

The specific connection order of the convolutional blocks is a 3×3 convolutional layer, a batch normalization layer, a Relu activation function, a 3×3 convolutional layer, a batch normalization layer and a Relu activation function. Each down-sampling uses a max-pooling with a stride of 2 to make the feature map size become half of the original image, and the number of feature map channels become twice of a number of feature map channels of the original image to compensate for the loss of information. Up-sampling uses bilinear interpolation to double the size of the image, that is, double the resolution.

The four branches of the dilated convolution module use convolution kernels with different expansion rates to extract feature map information at different scales. Each branch ends with 1×1 convolution to control the number of feature map channels of each scale to achieve cross-channel fusion and information integration, and the feature mapping after stitching of different features is guaranteed to have the same dimension as the feature mapping of the input module.

In a decoding process of the multi-feature fusion segmentation network, each decoder layer is connected to a feature mapping of shallow and same layer from an encoder via an Dilated Convolution Module to obtain the detailed information of shallow layer of different receptive fields, and combine with the deep semantics to improve the segmentation accuracy of the segmentation target with different sizes.

Figure 3:
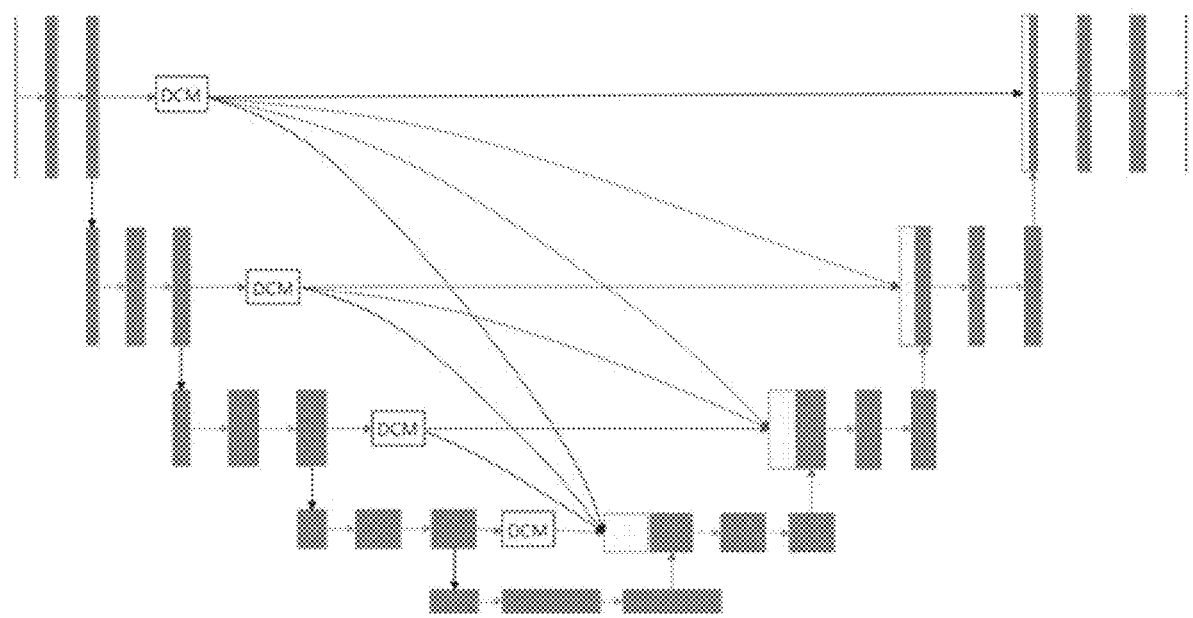
FIG. 3 is a schematic diagram of a structure of a segmentation network in the method of the present disclosure.
Figure 4:
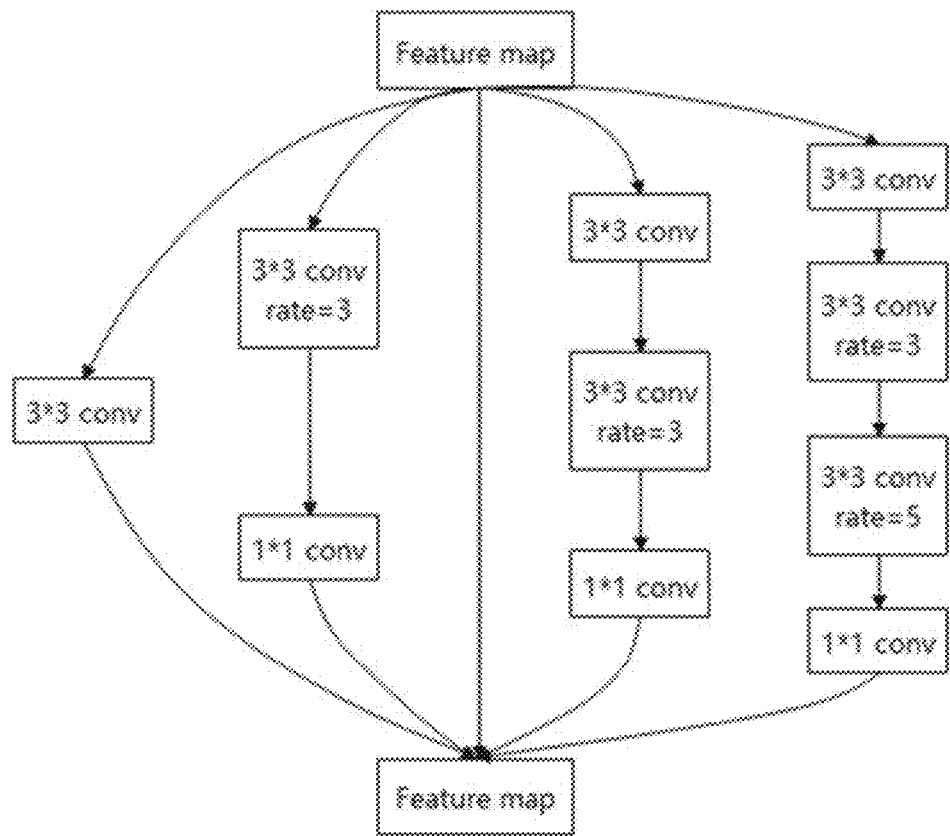
FIG. 4 is a schematic diagram of a Dilated Convolution Module for multi-feature fusion in the present disclosure.

On the original U-net basic network, an Dilated Convolution Module is added after each convolutional block in the encoding part. The specific connection of the Dilated Convolution Module is shown in FIG. 3, 3×3 convolutional kernels with different dilate rates are connected in parallel, the feature maps of different receptive fields are captured by each branch, and then the number of channels are adjusted by using 1×1 convolution, so that the input and output feature mapping of the module have the same dimensions, so as to ensure that the feature mapping are the same as those of the decoding part during fusion.

In addition to the original skip connection of U-Net between the same stage, the connections between the stages of the decoding part and the lower or horizontal stages of the encoding part are increased to fuse deep semantic information and shallow detailed formation The connections can bridge the semantic gap caused by the large splicing span and keep more of the underlying information.

The segmentation network includes feature extraction and revolution enhancement, the purpose of which is to reduce semantic gaps and fuse deep and shallow semantic features. The training is stopped when the loss function reaches a minimum.

The step 5 is specifically implemented as follows: the loss function of segmentation network based on multi-feature fusion is set up.

In the segmentation network part, the loss function is set as the dice coefficient commonly used in medicine, and the specific formula is:

$$Dice = \frac{2|A \cap B|}{|A| + |B|},$$

wherein, $|A \cap B|$ represents common elements between set A and set B, $|A|$ represents a number of elements in the set A, $|B|$ represents a number of elements in the set B, and the elements in the set A is the segmented image obtained by segmenting the input data set by the multi-feature fusion segmentation network, elements in the set B are the real segmentation image of the target area in the original image.

In order to calculate the set similarity measurement function of the predicted real segmentation image, the $|A|+|B|$ is approximated as a point multiplication between an actual segmented image and the real segmentation image; and all element values in the set A and set B are added. When the loss function is minimized, the training is stopped to obtain the trained segmentation network model. In order to calculate the dice coefficient of the predicted segmentation image, $|A|+|B|$ is approximated as the point multiplication between the predicted image and the label, and the elements in the set A and the set B are added.

Step 7, the segmentation network is trained.

In order to minimize the loss function in step 5, the Adam optimizer is used to initialize the weight parameters of the network in each stage first, and the weight parameters are randomly initialized with a Gaussian distribution with an average value of 0.

For each sample image x, the forward propagation is first used to calculate the total error, and then the back propagation is used to calculate the partial derivative of each weight parameter; finally, the weight parameters are updated according to the gradient descent method. This step is repeated until the loss function reaches the minimum, and a trained segmentation network model is obtained.

Step 8, the fundus blood vessel image to be segmented is input into the segmentation network of the present disclosure to obtain a segmented fundus blood vessel image.

When segmenting the fundus blood vessel data set, the generative adversarial network is used to expand the DRIVE data set. By training a generator that can generate fundus-like blood vessel images, the problem of inaccurate segmentation caused by over-fitting in the training process due to the small data set of medical images is alleviated. At the same time, in the process of generating fake images with segmentation labels, the one-to-one relationship between labels and images is maintained, which provides favorable conditions for final evaluation. By improving the original U-Net structure, the present disclosure solves the problem of loss of shallow detail information in the down-sampling process. The increased multi-scale Dilated Convolution Module improves the fusion of deep and shallow semantics, reduces the semantic gap. The segmentation targets of different scales are extracted effectively, which improves the segmentation accuracy of foreground and background of medical images.

The above are only the preferred embodiments of the present disclosure. It should be pointed out that for those of ordinary skill in the art, without departing from the technical principles of the present disclosure, several improvements and modifications can be made. These improvements and modifications should also fall within protection scope of the present disclosure.

The invention claimed is:

1. A medical image segmentation method based on a U-Net, comprising following steps:
step 1: selecting a medical image data set from existing medical image database;
step 2: obtaining paired original image and manual segmentation label of a target area in the original image from the medical image data set; and generating, by the real segmentation map, a composite image based on a generator G;
sending the composite image to a discriminator D for discrimination; and discriminating, by the discriminator D, whether the composite image comes from the medical image data set, and outputting a probability that the composite image comes from the medical image data set;
step 3: importing the paired original image and the real segmentation map of the target area in the original image into a generative adversarial network to train the generative adversarial network to obtain a generator model; wherein a generative adversarial joint loss function of the generative adversarial network is:

$$\mathcal{L}(G,D)=E_{x,y}[\log D(x,y)]+E_{x,z}[\log(1-D(x,G(x,z))],$$

wherein, x is the real segmentation map of the original image, y is the original image, z is random noise, E[*] represents an expected value of a distribution function, and D(x,y) is an output probability of the discriminator D when input is x and y, G(x,z) is the composite image;
increasing distance loss of L1 to constrain a difference between the composite image and the original image and reduce fuzz:

$$\mathcal{L}_{L1}(G)=E_{x,y,z}[\|y-G(x,z)\|_1];$$

step 4: using the generator model trained in step 3 to generate the composite image; wherein the composite image and the original image are used as an input data set of a multi-feature fusion segmentation network; and dividing the input data set into a training set and a testing set;
step 5: training the multi-feature fusion segmentation network by using the input data set in step 4 to obtain a segmentation network model; wherein, in a decoding process of the multi-feature fusion segmentation network, each decoder layer is connected to a feature mapping of shallow and same layer from an encoder via an Dilated Convolution Module;
step 6: inputting the original image to be segmented into the trained segmentation network model for segmentation to obtain an actual segmentation image output by the model.

2. The medical image segmentation method of claim 1, wherein,
in step 3, the training of the generative adversarial network comprises a training of the generator G and a training of the discriminator D; a forward propagation and backward propagation of neural network are used to alternately train the discriminator D and the generator G by gradient descent method until a probability that the composite image generated by the generator G is a real image is identified by the discriminator D as 0.5, the training is completed, and the generator model and a discriminator model are obtained.

3. The medical image segmentation method of claim 1, wherein,
in step 5, the multi-feature fusion segmentation network comprises feature extraction and resolution enhancement; the feature extraction comprises five convolutional blocks and four down-sampling, and the convolutional blocks are connected by the down-sampling; the resolution enhancement comprises four convolutional blocks connected by up-sampling.

4. The medical image segmentation method of claim 1, wherein,
step 5 comprises following steps:
in the multi-feature fusion segmentation network, setting the loss function as a set similarity measurement function, and a specific formula is $$Dice=\frac{2|A\cap B|}{|A|+|B|},$$

wherein, |A∩B| represents common elements between set A and set B, |A| represents a number of elements in the set A, |B| represents a number of elements in the set B, and the set A is a segmented image obtained by segmenting the input data set by the multi-feature fusion segmentation network, elements in the set B are the real segmentation image of the target area in the original image;
approximating the |A∩B| as a point multiplication between an actual segmented image and the real segmentation image to calculate a set similarity measurement function of a predicted real segmentation image;
adding all element values in a result of the point multiplication; stopping training when the loss function is minimum, and obtaining the trained segmentation network model.

5. The medical image segmentation method of claim 3, wherein,
   the generator G is a codec structure, in which residual blocks of same level are skip connected in a manner like U-net; the generator G comprises 9 residual blocks, 2 down-sampled convolutional layers with a stride of 2, and 2 transposed convolutions;
   after all non-residual blocks, a batch normalization function and a Relu function are executed; the discriminator D uses Markovian discriminator model which is same as patchGAN.

6. The medical image segmentation method of claim 3, wherein,
   a connection sequence in the convolutional block is a 3×3 convolutional layer, a batch normalization layer, a Relu activation function, a 3×3 convolutional layer, a batch normalization layer, and a Relu activation function; each down-sampling uses a max-pooling with a stride of 2, a feature map size of the original image after the convolutional layer becomes half of a feature map size of the original image before down-sampling, and a number of feature map channels of the original image becomes twice a number of feature map channels of the original image before down-sampling; up-sampling uses bilinear interpolation to double a resolution of the feature map of the original image;
   in all convolutional layers, first and last convolutional layers use 7×7 convolutional kernels, and other convolutional layers use 3×3 convolutional kernels; the 7×7 convolutional kernels use separable convolution to reduce parameters of the segmentation network model and calculation amount of the segmentation network model.

7. The medical image segmentation method of claim 2, wherein,
   the step of slopping training when the loss function is minimized, and obtaining a trained segmentation network model, comprises following steps:
   initializing weight parameters of the multi-feature fusion segmentation network at each stage based on Adam optimizer, and randomly initializing the weight parameters by using a Gaussian distribution with an average value of 0;
   for each sample image in the training set input in the segmentation network model, calculating a total error between the real segmentation image and the real segmentation map of the target area in the original image by using the forward propagation first; then calculating partial derivative of each weight parameter by using the backward propagation of the neural network; and finally updating the weight parameter according to the gradient descent method; and repeating above steps to minimize the loss function to obtain the trained segmentation network model; wherein
   the sample image comprises the composite image and the original image.

8. The medical image segmentation method of claim 1, wherein the input data set used as the multi-feature fusion segmentation network together with the original image is divided into the training set and the testing set in a ratio of 7:3.

* * * * *